United States Patent [19]

Erczi et al.

[11] Patent Number: 4,731,383

[45] Date of Patent: Mar. 15, 1988

[54] AMINOGUANIDINE COMPOUNDS, THEIR COMPOSITIONS AND PHARMACEUTICAL USES

[75] Inventors: Istvan Erczi; Jeno Marosfalvi; Gyorgy Rabloczky; Andras Varro; Maria Kuhar nee Kurthy; Istvan Elekes; Laszlo Szatmary; Laszlo Jaszlits, all of Budapest, Hungary

[73] Assignee: Biogal Gyogyszergyar, Debrecen, Hungary

[21] Appl. No.: 925,489

[22] Filed: Oct. 29, 1986

Related U.S. Application Data

[63] Continuation of Ser. No. 680,915, Dec. 12, 1984.

[30] Foreign Application Priority Data

Dec. 12, 1983 [HU] Hungary ............................... 4222/83

[51] Int. Cl.$^4$ ..................... A61K 31/55; C07C 133/10
[52] U.S. Cl. .................................. 514/634; 514/212; 514/237; 514/255; 514/331; 514/408; 540/610; 544/165; 544/167; 544/403; 546/246; 564/228
[58] Field of Search ................ 564/228; 514/634, 212, 514/237, 255, 331, 408; 540/610; 544/165, 167, 403; 546/246

[56] References Cited

U.S. PATENT DOCUMENTS 3,803,324  4/1974  Winter et al. ........................ 514/634

FOREIGN PATENT DOCUMENTS 1939738  2/1971  Fed. Rep. of Germany ...... 514/634

OTHER PUBLICATIONS

Szerekes, L. et al., *Experimental Cardiac Arrhythmias and Anti-arrhythmic Drugs*, (1971) pp. 72–74, Academic Press, Budapest.

Vargaftig, B. et al., *European J. of Pharm.* (1969), vol. 6, pp. 49–55.

Litchfield, J. T. et al., *J. Pharm. Exp. Ther.*, vol. 96 (1949), pp. 99–113.

*Primary Examiner*—Donald B. Moyer
*Assistant Examiner*—L. Hendriksen
*Attorney, Agent, or Firm*—Keil & Weinkauf

[57] ABSTRACT

The invention relates to new aminoguanidine derivatives of the general formula (I),

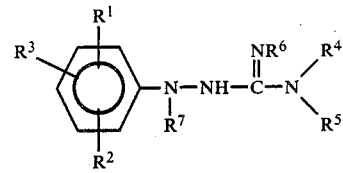

wherein
$R^1$, $R^2$ and $R^3$ each represent hydrogen or halogen atom, $C_{1-4}$ alkyl, nitro, trifluoromethyl or $C_{1-4}$ alkoxy group,
$R^4$ and $R^5$ represent a $C_{1-4}$ alkyl group, furthermore $NR^4R^5$ may form a 5 to 7 membered saturated heterocyclic group containing either one or two nitrogen atoms or a nitrogen and an oxygen atom and being optionally substituted by one or two methyl, hydroxymethyl or hydroxyethyl groups,
$R^6$ and $R^7$ each represent a hydrogen atom, normal or branched $C_{1-4}$ alkyl or $C_{2-4}$ alkenyl group, and to their pharmaceutically acceptable acid addition salts as well as to a process for the preparation thereof.

The new compounds of the invention possess valuable antiarrhythmic activity and are devoid of the undesired circulatory side effects of the known antiarrhythmic compounds.

12 Claims, No Drawings

AMINOGUANIDINE COMPOUNDS, THEIR COMPOSITIONS AND PHARMACEUTICAL USES

This application is a continuation of application Ser. No. 680,915, filed on Dec. 12, 1984.

The invention relates to new aminoguanidine derivatives of the formula (I),

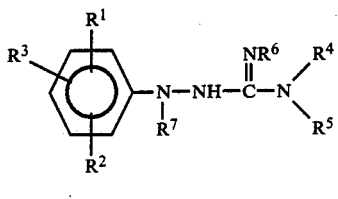

wherein
$R^1$, $R^2$ and $R^3$ each represent hydrogen or halogen atom, $C_{1-4}$ alkyl, nitro, trifluoromethyl or $C_{1-4}$ alkoxy group, $R^4$ and $R^5$ represent a $C_{1-4}$ alkyl group, furthermore $NR^4R^5$ may form a 5 to 7 membered saturated heterocyclic group containing either one or two nitrogen atoms or a nitrogen and an oxygen atom and being optionally substituted by one or two methyl, hydroxymethyl or hydroxyethyl groups, $R^6$ and $R^7$ each represent atom, normal or branched $C_{1-4}$ alkyl or $C_{2-4}$ alkenyl group,
and to their pharmaceutically acceptable acid addition salts as well as to a process for the preparation thereof.

Several aminoguanidine derivatives are described in the literature. The 1-aryloxy-alkyl-aminoguanidine derivatives are adrenergic neuron blocking agents (J. Med. Chem. 10, 391/1967/), the 1,1-dialkyl-aminoguanidine derivatives are pesticides (published South African patent application No. 69 03,667), while the 1-phenyl-alkyl-aminoguanidines (Neth. patent application No. 6,505,684 and J. Med. Chem. 13, 1051/1970/), 4-phenyl-aminoguanidines (published German patent application No. 2,452,691 and U.S. Pat. No. 4,101,675) and 1-phenyl-4-monoalkyl-aminoguanidines (published South African patent application No. 69 04,823) are antihypertensive agents.

The new compounds of formula (I) of the invention—the 1-phenyl-4,4-disubstituted-aminoguanidine derivatives—are different in structure from the known 1-phenyl-aminoguanidine derivatives, and affect favourably the rhythmic disorders of the heart, i.e. they are potent antiarrhythmic agents.

The compounds of formula (I) are prepared according to the invention either by a. reacting a phenylhydrazine derivative of formula (II)

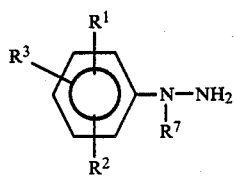

wherein $R^1$, $R^2$, $R^3$ and $R^7$ are defined as above, or its acid addition salt, with either an N,N-disubstituted-cyanamide of formula (III),

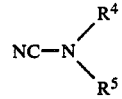

wherein $R^4$, $R^5$ or $NR^4R^5$ are as defined above, or with an isothiourea derivative of formula (IV),

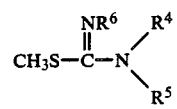

wherein $R^4$, $R^5$ or $NR^4R^5$ and $R^6$ are as defined above or with its acid addition salt; or b. reacting an isothiosemicarbazide derivative of formula (V),

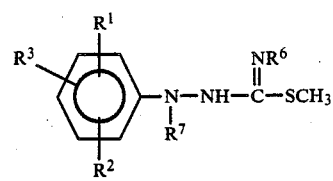

wherein $R^1$, $R^2$, $R^3$, $R^6$ and $R^7$ are as defined above or its acid addition salt, with a secondary amine of formula (VI),

wherein $R^4$, $R^5$ or $NR^4R^5$ are as defined above, or with its acid addition salt, and, if desired, the free base of the formula (I) is liberated from its salt and/or is converted into its acid addition salt by a pharmaceutically acceptable acid.

The tautomers of the above compounds as well as mixtures thereof prepared either by method a. or b. are within the scope of the invention.

According to a preferred variant of method a. of the invention 1.0M of the phenylhydrazine derivative of formula (II) or its salt, preferably its hydrohalogenide, is reacted with 1.1 to 1.25M of the cyanamide derivative of formula (III), or with 1.0M of the isothiourea derivative of formula (IV) or its salt, preferably its hydrohalogenide, in an inert solvent, in a temperature range of 80° to 160° C., preferably at 90° to 130° C., under nitrogen gas. Cyclohexanol, or $C_{2-6}$ normal or branched aliphatic alcohols, i.e. ethanol, n-propanol, i-propanol, n-butanol, amylalcohol or hexylalcohol, are preferred solvents for the reaction. Depending on the solvent and temperature applied the reaction time may amount to 3–72 hours.

According to an other variant of method a. of the invention the starting materials are melted under nitrogen, preferably at 100° to 130° C. In the reaction of the compounds of formula (II) and (IV) the starting materials are cautiously melted at 110° C. under nitrogen flow, and the melted mixture is stirred for several hours at 130° C. As during the condensation reaction methylmercaptan gas is formed, the end of the reaction can be recognised by the end of gas formation. In the reaction of the compounds of formulas (II) and (III) the progress of the reaction can be monitored by thin-layer chromatography.

According to the preferred method b. of the invention 1M of the thiosemicarbazide salt of formula (V), preferably its hydrobromide or hydroiodide, is reacted with 1M of a secondary amine of formula (VI), or 1M of the thiosemicarbazide of formula (V) is reacted with a salt of the secondary amine of formula (VI), preferably its hydrochloride, either in the presence or the absence of a solvent, in a temperature range of 20° to 130° C., for 3 to 72 hours. The solvents applied in variant a. of the process can preferably be used. The reaction temperature of the reaction in melt, performed in the absence of any solvent, is preferably 110° to 130° C. The end of the reaction can be recognized by the end of methylmercaptan gas formation.

In the reaction, performed in a solvent according to either of the process variants, the product formed is precipitating in most of the cases from the reaction mixture upon cooling, and can be separated by filtration. In those cases where the product formed fails to precipitate from the solution upon cooling, its precipitation can be induced by the addition of hexane, ether or acetone. In the reactions carried out in melt the cooled melt is dissolved in ethanol, the insoluble part is filtered, and the product is precipitated from the filtrate by the addition of hexane, ether or acetone. The raw product is purified similarly.

If the acid addition salt of the starting material is applied, in the reaction the acid addition salt of the target product is formed. The base can be set free therefrom with an inorganic or organic base, preferably with solid sodium hydrocarbonate or aqueous triethylamine. If desired, the base can be converted into various other acid addition salts with a suitable organic or inorganic acid.

The starting materials of general formulas (II), (III), (IV), (V) and (VI) as well as the processes for their preparation are known from the literature [J. Am. Chem. Soc. 81, 4678 (1959); American Chem. J. 42, 23, Zeitschrift für Elektrochemie 22, 342; J. Am. Chem. Soc. 72, 4699 (1950)].

In the process of the invention the following starting phenylhydrazines of general formula (II) or their salts are preferably used: phenylhydrazine, 2-methyl-, 4-methyl-, 2-chloro-, 3-chloro-, 4-chloro-, 2-trifluoromethyl-, 3-trifluoromethyl-, 2-methoxy-, 2,3-dimethyl-, 2,4-dimethyl-, 2,5-dimethyl-, 2,6-dimethyl-, 2-methyl-6-ethyl-, 2,4,6-trimethyl-, 2-methyl-3-chloro-, 2-methyl-4-chloro-, 2-methyl-6-chloro-, 2,5-dichloro-, 2,6-dichloro-, 2-methoxy-, 3,4-dimethoxy-, and 4-nitrophenylhydrazine as well as α-methyl-, α-i-propyl- and α-allyl-phenylhydrazine.

In the process of the invention the following N,N-disubstituted-cyanamides of formula (III) are preferably applied as starting materials: dimethyl-cyanamide, diethyl-cyanamide, 1-cyano-pyrrolidine, 1-cyano-piperidine, 1-cyano-2-methyl-, 1-cyano-3-methyl-piperidine, 4-cyano-1-methyl-, 4-cyano-2,6-dimethyl-, 4-cyano-1-(2-hydroxyethyl)-piperazine, 4-cyano-, 4-cyano-2-methyl-, 4-cyano-2,6-dimethylmorpholine and 1-cyano-hexahydro-azepine.

The following S-methyl-isothioureas of formula (IV) and their salts can preferably be used as starting materials: N,N,S-trimethyl-isothiourea, N,N-diethyl-S-methyl-isothiourea, N,N-tetramethylene-S-methylisothiourea, N,N-pentamethylene-S-methyl-isothiourea, N,N,N',S-tetramethyl-isothiourea and N,N-diethyl-N',S-dimethyl-isothiourea.

The following isothiosemicarbazide derivatives of formula (V) and their salts can preferably be used as starting materials: 2-methyl-phenyl-S-methyl-, 2-chloro-phenyl-S-methyl-, 3-chloro-phenyl-S-methyl-, 2,6-dichloro-phenyl-S-methyl-, 2,6-dimethyl-phenyl-S-methyl-, 2-methyl-phenyl-N,S-dimethyl-, 2-chloro-phenyl-N,S-dimethyl-, 2,6-dimethyl-phenyl-N,S-dimethyl-, 2,6-dichloro-phenyl-N,S-dimethyl-isothiosemicarbazide.

The following secondary amines of formula (VI) and their salts can preferably be used as starting materials: dimethylamine, diethylamine, pyrrolidine, piperidine, 2-methyl-, 3-methyl-piperidine, N-methyl-, 2,6-dimethyl-, N-(2-hydroxyethyl)-piperazine, morpholine, 2-methyl-, 2,6-dimethyl-morpholine, hexamethyleneimine.

The 1-phenyl-aminoguanidine derivatives of formula (I) exhibit high antiarrhythmic activity in mouse, cat, guinea pig and dog. In several tests, in doses of 10-50-100 mg/kg, this antiarrhythmic effect is significant and stable both at parenteral and oral administration.

The antiarrhythmic activity was tested by the following methods:

1. Aconitin-induced arrhythmia in mice

Arrhytmia was induced in male mice, weighing 20 to 25 g, by treating them continuously, at a rate of 0.2 ml/min with an infusion containing 5 μg/kg of aconitin. The test compound was administered to the animals either intraperitoneally (by injecting it into the abdominal cavity) 15 minutes before the start of the infusion, or orally 60 minutes before the onset of the infusion. The time of the appearance of arrhythmia was recorded, and the percentage of delay was calculated in relation to the data obtained in the controls, pretreated with 0.9 percent sodium chloride solution only [B. Vargaftig and J. L. Coignet: European J. of Pharmacol. 6, 49 to 55 (1969); N. K. Dadkar and B. K. Bhattachariya: Arch. Int. Pharmacodyn. 212, 297 to 301 (1974); D. U. Nwagwu, T. L. Holcslaw and S. J. Stohs: Arch. Int. Pharmacodyn. 229, 219 to 226 (1977)].

The results are presented in Tables 1 and 2. 1-(2,6-Dimethylphenoxy)-2-aminopropane hydrochloride (Mexiletin) and/or quinidine were applied as reference substances. The actute toxicity values ($LD_{50}$) were calculated according to the method of Litchfield and Wilcoxon [J. Pharmacol. Exp. Ther., 96, 99 to 113 (1949)].

TABLE 1

Examination of the antiarrhythmic effect in anesthesized mice treated with aconitin, with intraperitoneal administration of the test compounds

| Compound Example No. | Dose mg/kg i.p. | Delay in the appearance time of arrhythmia % | Number of animals n | $LD_{50}$ mg/kg i.p. |
|---|---|---|---|---|
| 1 | 25 | +164 | 18 | 81 |
|   | 50 | +174 | 18 |   |
| 2 | 25 | +79 | 16 | 73 |
|   | 50 | +156 | 16 |   |
| 3 | 10 | +108 | 12 |   |
|   | 20 | +68* | 12 |   |
| 4 | 5 | +28 | 5 |   |
|   | 10 | +77* | 9 |   |
| 5 | 25 | +113 | 20 | 130 |
|   | 50 | +155 | 20 |   |
| 6 | 50 | +114 | 6 |   |

TABLE 1-continued

Examination of the antiarrhythmic effect in anesthesized mice treated with aconitin, with intraperitoneal administration of the test compounds

| Compound Example No. | Dose mg/kg i.p. | Delay in the appearance time of arrhythmia % | Number of animals n | LD$_{50}$ mg/kg i.p. |
|---|---|---|---|---|
| 7 | 25 | +50 | 10 | |
|   | 50 | +128 | 20 | |
| 8 | 5 | +32 | 6 | |
|   | 10 | +110* | 7 | |
| 9 | 50 | +171 | 12 | |
| 15 | 50 | +67 | 6 | |
| 21 | 25 | +110 | 6 | |
|   | 50 | +86** | 9 | |
| 22 | 50 | +100 | 20 | |
| Reference substance: 1-(2,6-di-methyl-phenoxy)-2-amino-propane HCl (Mexiletin) | 5 | +3.5 | 20 | 114 |
|   | 10 | +7.7 | 20 | |
|   | 25 | +33 | 20 | |
|   | 50 | +83 | 20 | |
|   | 75 | +162 | 16 | |

*compound is toxic in higher doses
**compound is toxic in higher doses and induces bradycardia

TABLE 2

Examination of the antiarrhythmic effect in anesthesized mice treated with aconitin, with oral administration of the test compounds

| Compound Example No. | Dose mg/kg p.o. | Delay in the appearance time of arrhythmia % | Number of animals n | LD$_{50}$ mg/kg p.o. |
|---|---|---|---|---|
| 1 | 50 | +102 | 5 | 203 |
|   | 100 | +197 | 14 | |
| 2 | 25 | +39 | 15 | 220 |
|   | 50 | +71 | 5 | |
|   | 100 | +150 | 5 | |
| 5 | 100 | +111 | 20 | 400 |
| 6 | 100 | +70 | 6 | |
| 7 | 50 | +54 | 6 | |
|   | 100 | +137 | 8 | |
| 18 | 100 | +74 | 6 | |
| Reference substance: Mexiletin | 100 | +93 | 20 | 390 |

2. Determination of the fibrillation threshold in anaesthesized cats

The chests of the cats were opened under chloralose-urethane anaesthesia, a bipolar stimulating electrode was fixed onto the heart, and the heart was stimulated electrically with a frequency of 20 Hz, under continuously increasing current strength, until a fibrillo-flattern could be observed. This current strength was considered as the fibrillation threshold of the animal. Thereafter the test compounds were administered, and the increase in the fibrillation threshold value was recorded at i.v. and intraduodenal (i.d.) administration (Szekeres and Papp: Experimental Cardiac Arrhythmias and Antiarrhythmic Drugs, Academic Press, Budapest, 1971).

The values are presented in Tables 3 and 4.

TABLE 3

Effect of the test compounds on the fibrillation threshold measured in anaesthesized cat at i.v. administration

| Compound Example No. | Dose mg/kg i.v. | Percentual change in the fibrillation threshold | | |
|---|---|---|---|---|
| | | 2 min | 10 min | 20 min |
| | | following treatment | | |
| 5 | 0.5 | +18.75 | +40.75 | +37.6 |
|   | 1.0 | +35.2 | +55.2 | +48.4 |
|   | 2.0 | +101.1 | +93.0 | +94.15 |
|   | 4.0 | +153.3 | +125.65 | +124.0 |
|   | 8.0 | +392.8 | +354.5 | +310.25 |
| 11 | 2.0 | +130.6 | +149.0 | +163.3 |
|   | 4.0 | +176.0 | +328.0 | +316.0 |
| Mexiletin | 10.0 | — | +161.2 | +92.0 |

TABLE 4

Effect of the test compounds on the fibrillation threshold measured in anaesthesized cats at i.d. administration

| Compound Example No. | Dose mg/kg i.d. | No. of animals n | Percentual change in the fibrillation threshold | | | | | | | | | |
|---|---|---|---|---|---|---|---|---|---|---|---|---|
| | | | 10 | 20 | 30 | 40 | 50 | 60 | 70 | 80 | 90 | 100 |
| | | | minutes following treatment | | | | | | | | | |
| 5 | 20 | 7 | +22.2 | +29.0 | +94.0 | +103.7 | +100.4 | +105.8 | +100.3 | +121.5 | +132.8 | +132.3 |
| 11 | 20 | 4 | +5.8 | +22.0 | +43.8 | +79.6 | +115 | +118 | +141 | +198 | +209.5 | +272.5 |
| Quinidine | 10 | 5 | +0.4 | +26.7 | +58.5 | +48.5 | +32.1 | +20.8 | +9.5 | +8.8 | +3.8 | 0.0 |

3. Electrophysiological tests performed in the isolated rabbit heart

Hearts of rabbits of both sexes, weighing 1 to 2 kg, were removed, the right and left auricles and a segment of the right ventricle were prepared and placed into a vessel filled with nutrient solution. Bipolar platinum electrodes (a stimulating electrode and a lead electrode) were placed on the organ strips, and the electric stimulus threshold and the speed of impulse conduction were measured. The effective refractory period was determined on the basis of the maximal driving frequency. The results were read from the screen of an oscilloscope (Szekeres and Papp: Experimental Cardiac Arrhythmias, Academic Press, Budapest, 1971).

The electrophysiological activities of the compounds of the invention are demonstrated on the example of 1-(2-methylphenyl)-4,4-dimethyl-aminoguanidine hydrochloride (Example 1). The test results are presented in Table 5.

The Table shows that the conduction time in both the left auricle and the right ventricle is prolonged dose-dependently by the compound of the invention, which means a reduction of the speed of impulse conduction. It decreases the maximal driving frequency, indicating a prolongation of the refractory period. The auricular contractility is dose dependently, though moderately reduced by the compound.

TABLE 5

Electrophysiological effect in the isolated rabbit heart

| Test parameters | Compound Example No. | 0.25 mg/l | 0.5 mg/l | 1.0 mg/l | 2.0 mg/l | 4.0 mg/l | 8.0 mg/l |
|---|---|---|---|---|---|---|---|
| *Percentual dose responses measured in the right ventricle n = 4* | | | | | | | |
| Change in conduction time | 1 Mexiletin | +0.2 | +3.31 | +14.84 | +36.75 / +11 | +52.45 | +77.82 |
| Change in electric stimulus threshold | 1 Mexiletin | 0 | −1.43 | +5.42 | +20.6 / +6 | +23.6 | +35.8 |
| Change in max. driving frequency | 1 Mexiletin | −0.88 | −0.38 | −1.82 | −10.33 / −28 | −17.43 | −36.8 |
| *Percentual dose responses measured in the left auricle n = 4* | | | | | | | |
| Change in conduction time | 1 Mexiletin | +0.54 | +8.66 | +12.55 | +28.42 / +24 | +47.87 | +114.03 |
| Change in electric stimulus threshold | 1 Mexiletin | 0 | −1.82 | −11.8 | +30.84 / 36 | +43.4 | +83.9 |
| Change in max. driving frequency | 1 Mexiletin | −0.08 | −0.98 | −9.21 | −17.09 / −32 | −28.82 | −59.1 |
| Contractility | 1 | −2.61 | −7.57 | −15.5 | −18.12 | −27.08 | −37.92 |

It appears from the above tables that the compounds of the invention are similar or occasionally even superior in antiarrhythmic activity to the presently applied 1-(2,6-dimethylphenoxy)-2-amino-propane hydrochloride (Mexiletin). As an additional advantage, the compounds are devoid of the undesirable circulatory side effects, generally appearing upon the administration of the known antiarrhythmic agents, i.e. they fail to induce a pressure drop in the systemic circulation and a pressure increase in the pulmonary circulation in animals with intact chest or in unanaesthesized, permanently cannulated animals, at a dose range of 0.5 to 4.0 mg/kg. The antiarrhythmic effect of the compounds is not accompanied by any other activity affecting the vegetative nervous system, i.e. the compounds have neither alpha- nor beta-adrenergic blocking, nor adrenergic neurone blocking or parasympatholytic activity.

In addition, the compounds possess significant cardioprotective potency, i.e. their antiarrhythmic activity is also exhibited in the ischemic heart. This cardioprotective effect is three times higher than that of diethylamino-acet-(2,6-dimethyl)-anilide (Lidocain).

The compounds of the invention can be converted to pharmaceutical preparations by methods known in the art by applying additives, carriers and vehicles generally used in drug manufacturing.

A daily dose of 75 mg is planned for the treatment of human subjects weighing about 70 kg.

The following Examples are illustrating but not limiting the scope of the invention.

EXAMPLE 1

1-(2-Methylphenyl)-4,4-dimethyl-aminoguanidine hydrochloride

Method a.

A mixture of 1.59 g (0.01M) of 2-methyl-phenylhydrazine hydrochlorid, 3 ml of anhydrous n-propanol and 1 ml (0.0125M) of dimethyl-cyanamide is heated at 130° C. for 5 hours at continuous stirring and under nitrogen gas flow. To the resulting solution which is cooled to 0° C., 15 ml of hexane are added portion-wise. The precipitated white product is filtered on a glass filter, washed with a 4:1 mixture of hexane-ethanol and is dried. Yield 1.45 g (63.4 percent) of the product, m.p. 219° to 221° C.

Method b.

The procedure described under Method a. is applied except that n-butanol is used as solvent. Yield 1.33 g (58.2 percent) of the product, m.p. 219° to 221° C.

Method c.

The procedure described under Method a. is applied except that cyclohexanol is used as solvent. Yield 1.37 g (60.1 percent) of the product, m.p. 219° to 221° C.

Method d.

The procedure described under Method a. is applied except that the reaction is carried out without solvent, at 110° C. in a melted form. The resulting melt is suspended in a 4:1 mixture of hexane-ethanol, then it is filtered and dried. Yield 1.28 g (55.9 percent) of the product, m.p. 219° to 221° C.

EXAMPLE 2

1-(2,6-Dichlorophenyl)-4,4-dimethyl-aminoguanidine

The solution of 3.54 g (0.02M) of 2,6-dichlorophenyl-hydrazine, 6 ml of anhydrous n-propanol and 1.56 g (0.022M) of dimethyl-cyanamide is heated at 130° C. for 5 hours at continuous stirring and under nitrogen gas flow. The resulting solution is cooled to 0° C., then 60 ml of hexane are added portion-wise. The precipitated beige coloured product is filtered on a glass filter, it is washed with a 9:1 mixture of hexane-ethanol, and then dried. Yield 3.20 g (64.8 percent) of 1-(2,6-dichlorophenyl)-4,4-dimethyl-aminoguanidine, m.p. 153° to 154° C.

Preparation of the hydrochloride salt

The above base is dissolved in 10 ml of ethanol, then 10 ml of a saturated hydrochloric acid solution in ethanol are added to it dropwise at room temperature and at stirring. The resulting suspension is heated to 70° C. and it is stirred at this temperaturee for 30 minutes. The yellow solution is cooled to 40° C. and 80 ml of hexane are added to it at continuous stirring. The precipitated white product is filtered on a glass filter after cooling to 0° C., then it is washed with a 4:1 mixture of hexane-ethanol and dried. Yield 3.59 g (61.5 percent), m.p. 255° to 257° C.

EXAMPLE 3

1-(2-Chlorophenyl)-4,4-diethyl-aminoguanidine hydrochloride

The homogenized mixture of 2.14 g (0.015M) of 2-chloro-phenylhydrazine and 4.11 g (0.015M) of N,N-diethyl-S-methyl-isothiourea hydroiodide is cautiously melted at 110° C. under nitrogen flow. The melt is stirred for 1 hour at 110° C. and for 2 hours at 130° C. During the reaction methyl-mercaptan gas is liberated. When the gas formation has stopped, the dark red melt is cooled to room temperature, the solidified mass is dissolved in 15 ml of water, the solution is cooled to 0° C., the pH of this solution is adjusted to 8-9 with solid sodium hydrogencarbonate, then the precipitated beige-coloured crystals are filtered on a glass filter and washed with water having a temperature of 0° C. This wet product on the filter is dissolved in 25 ml of N hydrochloric acid at room temperature, the solution is decolourized with active carbon, then the solution is evaporated to dryness under reduced pressure. The evaporation residue is dissolved in 12 ml of anhydrous, hot ethanol, then it is cooled to 40° to 50° C., and portion-wise 50 ml of hexane are added to it. The precipitated white, crystalline plates are cooled to 0° C., filtered on a glass filter, washed with a 4:1 mixture of hexane and ethanol and dried. Yield 2.55 g (38.5 percent), m.p. 191.5° to 192.5° C.

EXAMPLE 4

1-(2-Methyl-phenyl)-4,4-diethyl-aminoguanidine hydrochloride 0.73 g (0.01M) of freshly distilled diethylamine is added to a solution of 3.23 g (0.01M) of 1-(2-methyl-phenyl)-3-(S-methyl)-isothiosemicarbazide hydroiodide in 10 ml of ethanol, and the solution is stirred at 40° C. for 72 hours. During the reaction methylmercaptan is generated. By the end of the reaction the solvent is evaporated at reduced pressure, the residue is dissolved in 10 ml of water, the solution is cooled to 0° C. and its pH is adjusted to 8-9 with solid sodium hydrogen carbonate. The precipitated beige-coloured product is filtered on a glass filter and washed with water having a temperature of 0° C. This wet material on the filter is dissolved in 13 ml of N hydrochloric acid at room temperature, the solution is decolourized with active carbon, and evaporated at reduced pressure to dryness. The evaporation residue is dissolved in a hot mixture of 10 ml of acetone and 2 ml of ethanol, the turbid solution is filtered, the filtrate is cooled to room temperature and 25 ml of ether are added to it. The precipitated, beige-coloured crystals are filtered on a glass filter following cooling to 0° C., washed with a 3:1 mixture of ether-acetone, and dried. Yield 0.95 g (37 percent), m.p. 174° to 176° C.

EXAMPLES 5 TO 54

The compounds presented in Table 6 can be prepared according to the procedures described in Examples 1 to 4. The Table lists the m.p. and the yield of the compounds, too.

TABLE 6

| Example No. | $R^1$ | $R^2$ | $R^3$ | $N{<}{R^4 \atop R^5}$ | $R^6$ | $R^7$ | Yield % | Hydrochloride M. p. °C. |
|---|---|---|---|---|---|---|---|---|
| 5 | 2-$CH_3$ | 6-$CH_3$ | H | $N(CH_3)_2$ | H | H | 61 | 258–260 |
| 6 | 2-Cl | H | H | $N(CH_3)_2$ | H | H | 69 | 252–253 |
| 7 | 2-$CH_3$ | H | H | 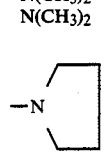 | H | H | 47 | 258–260 |
| 8 | 2-Cl | H | H | 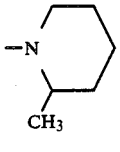 | H | H | 45 | 212–213 |
| 9 | H | H | 3-Cl | $N(CH_3)_2$ | H | H | 39 | 171–174 |
| 10 | 2-$CH_3$ | 6-$CH_3$ | H | $N(C_2H_5)_2$ | H | H | 42 | 212–215 |
| 11 | 2-$CH_3$ | 6-$CH_3$ | H | 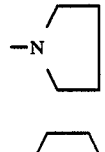 | H | H | 44 | 272–275 |
| 12 | 2-$CH_3$ | 6-$CH_3$ | H | 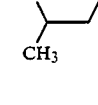 | H | H | 23 | 233–237 |

TABLE 6-continued

| Example No. | R¹ | R² | R³ | NR⁴R⁵ | R⁶ | R⁷ | Yield % | Hydrochloride M. p. °C. |
|---|---|---|---|---|---|---|---|---|
| 13 | 2-CF$_3$ | H | H | N(CH$_3$)$_2$ | H | H | 71 | 238–242 |
| 14 | 2-CF$_3$ | H | H | N(C$_2$H$_5$)$_2$ | H | H | 60 | 202–206 |
| 15 | 2-Cl | 2-Cl | H | N(CH$_3$)$_2$ | H | H | 63 | 257–258 |
| 16 | 2-CH$_3$ | 6-Cl | H | N(CH$_3$)$_2$ | H | H | 40 | 256–258 |
| 17 | 2-CH$_3$ | H | 3-CH$_3$ | N(CH$_3$)$_2$ | H | H | 42 | 239–242 |
| 18 | H | H | H | N(CH$_3$)$_2$ | H | H | 36 | 162–164 |
| 19 | H | H | 4-Cl | N(CH$_3$)$_2$ | H | H | 58 | 192–200 |
| 20 | 2-CH$_3$ | H | H | —N(piperazinyl)N—(CH$_2$)$_2$—OH | H | H | 75 | 245–247 |
| 21 | 2-CH$_3$ | 6-C$_2$H$_5$ | H | N(CH$_3$)$_2$ | H | H | 53 | 253–256 |
| 22 | 2-CH$_3$ | H | H | morpholino | H | H | 51 | 160–163 |
| 23 | 2-CH$_3$ | H | H | 2-methylpiperidino | H | H | 39 | 204–205 |
| 24 | 2-CH$_3$ | H | 3-Cl | N(CH$_3$)$_2$ | H | H | 50 | 260–264 |
| 25 | 2-CH$_3$ | 6-CH$_3$ | 4-CH$_3$ | N(CH$_3$)$_2$ | H | H | 16 | 248–251 |
| 26 | H | 5-CH$_3$O | 4-CH$_3$O | pyrrolidino | H | H | 31 | 206–207 |
| 27 | H | H | 4-NO$_2$ | N(CH$_3$)$_2$ | H | H | 68 | 258–260 |
| 28 | 2-CH$_3$O | H | H | N(CH$_3$)$_2$ | H | H | 39 | 95–97 |
| 29 | 2-CH$_3$ | 5-CH$_3$ | H | N(CH$_3$)$_2$ | H | H | 41 | 238–240 |
| 30 | 2-CH$_3$ | H | 4-CH$_3$ | N(CH$_3$)$_2$ | H | H | 52 | 219–222 |
| 31 | H | H | 4-CH$_3$ | N(CH$_3$)$_2$ | H | H | 12 | 176–179 |
| 32 | H | H | H | N(CH$_3$)$_2$ | H | CH$_3$ | 46 | 196–200 |
| 33 | H | H | H | N(CH$_3$)$_2$ | H | i-propyl | 58 | 95–105 |
| 34 | H | H | H | N(CH$_3$)$_2$ | H | allyl | 41 | 161–163 |
| 35 | 2-CH$_3$ | H | 4-Cl | N(CH$_3$)$_2$ | H | H | 45 | 252–256 |
| 36 | 2-CH$_3$ | 6-CH$_3$ | H | heptamethyleneimino | H | H | 26 | 260–265 |
| 37 | 2-CH$_3$ | H | H | hexamethyleneimino | H | H | 35 | 195–198 |
| 38 | 2-CH$_3$ | 6-CH$_3$ | H | 2,6-dimethylmorpholino | H | H | 40 | 276–281 |

TABLE 6-continued
| Example No. | R¹ | R² | R³ | NR⁴R⁵ | R⁶ | R⁷ | Yield % | Hydrochloride M. p. °C. |
|---|---|---|---|---|---|---|---|---|
| 39 | 2-CH₃ | H | H | 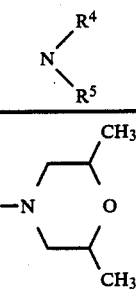 | H | H | 54 | 236–240 |
| 40 | H | H | H | N(C₂H₅)₂ | H | CH₃ | 32 | 198–200 |
| 41 | 2-CH₃ | 6-CH₃ | H | 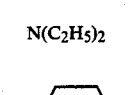 | H | H | 52 | 229–231 |
| 42 | 2-CH₃ | 6-CH₃ | H |  | H | H | 54 | 205–211 |
| 43 | 2-CH₃ | H | H | 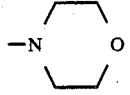 | H | H | 12 | 196–198 |
| 44 | 2-CH₃ | 6-CH₃ | H | 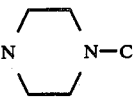 | H | H | 24 | 216–219 |
| 45 | 2-CH₃ | H | H | 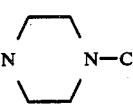 | H | H | 10 | 201–205 |
| 46 | 2-CH₃ | 6-CH₃ | H | 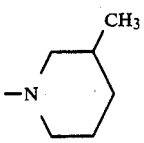 | H | H | 12 | 209–211 |
| 47 | 2-CH₃ | H | H | 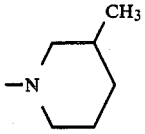 | H | H | 28 | 198–204 |
| 48 | 3-Cl | H | H | 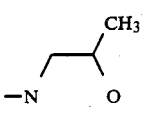 | H | H | 28 | 222–226 |
| 49 | 3-Cl | H | H | 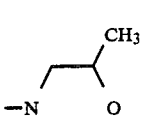 | H | H | 27 | 228–230 |

TABLE 6-continued

| Example No. | R¹ | R² | R³ | NR⁴R⁵ | R⁶ | R⁷ | Yield % | Hydrochloride M. p. °C. |
|---|---|---|---|---|---|---|---|---|
| 50 | 2-Cl | H | H | -N(CH(CH₃)CH₂)₂O (2,6-dimethylmorpholino) | H | H | 41 | 257-259 |
| 51 | 2-Cl | H | H | hexahydroazepino | H | H | 42 | 219-221 |
| 52 | 2-Cl | 6-Cl | H | pyrrolidino | H | H | 39 | 277-279 |
| 53 | 2-CH₃ | 6-CH₃ | H | 2,5-dimethylpiperazino | H | H | 18 | 286-287 dihydroxide |
| 54 | 2-Cl | H | H | 2-methylpiperidino | H | H | 35 | 224-226 |

What we claim is:

1. An aminoguanidine derivative of the formula (I),

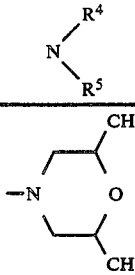

wherein
R¹, R² and R³ each represent hydrogen, halogen, $C_1$-$C_4$ alkyl, nitro, trifluoromethyl or $C_1$-$C_4$ alkoxy,
R⁴ and R⁵ represent $C_1$-$C_4$ alkyl, or NR⁴R⁵, is an unsubstituted morpholino, piperidino, pyrrolidino, piperazino or hexahydroazepino radical or a mono- or dimethyl substituted morpholino, piperidino or pipperazino or hydroxymethyl or hydroxyethyl substituted piperazino radical,
R⁶ and R⁷ each represent hydrogen, normal or branched $C_{1-4}$ alkyl or $C_{2-4}$ alkenyl,
and the pharmaceutically acceptable acid addition salts thereof.

2. 1-(2-Methyl-phenyl)-4,4-dimethyl-aminoguanidine hydrochloride.

3. 1-(2,6-Dichlorophenyl)-4,4-dimethyl-aminoguanidine hydrochloride.

4. 1-(2,6-Dimethyl-phenyl)-4,4-dimethyl-aminoguanidine hydrochloride.

5. A pharmaceutical composition having antiarrhythmic activity containing as active ingredient an effective amount of at least one compound of the formula (I)

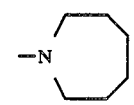

wherein
R¹, R² and R³ each represent hydrogen, halogen, $C_1$-$C_4$ alkyl, nitro, trifluoromethyl or $C_1$-$C_4$ alkoxy,
R⁴ and R⁵ represent $C_1$-$C_4$ alkyl, or NR⁴R⁵ is an unsubstituted morpholino, piperidino, pyrrolidino, piperazino or hexahydroazepino radical or a mono- or dimethyl substituted morpholino, piperidino or piperazino or hydroxymethyl or hydroxyethyl substituted piperazino radical,
R⁶ and R⁷ each represent hydrogen, normal or branched $C_{1-4}$ alkyl or $C_{2-4}$ alkenyl,
and the pharmaceutically acceptable acid addition salts thereof, and a conventional inert, non-toxic, solid or liquid carrier and/or additive.

6. A pharmaceutical composition as defined in claim 5, wherein the active ingredient is 1-(2-methylphenyl)-4,4-dimethyl-aminoguanidine hydrochloride.

7. A pharmaceutical composition as defined in claim 5, wherein the active ingredient is 1-(2,6-dichlorophenyl)-4,4-dimethyl-aminoguanidine hydrochloride.

8. A pharmaceutical composition as defined in claim 5, wherein the active ingredient is 1-(2,6-dimethylphenyl)-4,4-dimethyl-aminoguanidine hydrochloride.

9. A method of controlling arrhythmia in a patient suffering therefrom which comprises:
   administering to the patient an effective dose of a composition as defined in claim 5.

10. A method of controlling arrhythmia in a patient suffering therefrom which comprises:
    administering to the patient an effective dose of a composition as defined in claim 6.

11. A method of controlling arrhythmia in a patient suffering therefrom which comprises:
    administering to the patient an effective dose of a composition as defined in claim 7.

12. A method of controlling arrhythmia in a patient suffering therefrom which comprises:
    administering to the patient an effective dose of a composition as defined in claim 8.

* * * * *